United States Patent [19]

Haruna et al.

[11] Patent Number: 4,661,597

[45] Date of Patent: Apr. 28, 1987

[54] PROCESS FOR PREPARING 2,2,6,6-TETRAMETHYL-4-OXOPIPERIDINE

[75] Inventors: Tohru Haruna, Saitama; Atsushi Nishimura, Washinomiya; Kazuo Sugibuchi, Tokyo, all of Japan

[73] Assignee: Adeka Argus Chemical Co., Ltd., Urawa, Japan

[21] Appl. No.: 701,474

[22] Filed: Feb. 14, 1985

[30] Foreign Application Priority Data

Feb. 16, 1984 [JP] Japan .................................. 59-27711

[51] Int. Cl.[4] ........................................... C07D 211/74
[52] U.S. Cl. ................................................. 546/242
[58] Field of Search ........................................ 546/242

[56] References Cited

U.S. PATENT DOCUMENTS

| | | | |
|---|---|---|---|
| 3,513,170 | 5/1970 | Murayama et al. | 546/242 |
| 3,953,459 | 4/1976 | Orban et al. | 546/242 |
| 3,959,295 | 5/1976 | Orban et al. | 546/242 |
| 4,252,958 | 2/1981 | Hirai et al. | 546/242 |

*Primary Examiner*—John M. Ford
*Assistant Examiner*—Kurt G. Briscoe

[57] ABSTRACT

A process is provided for the preparation of 2,2,6,6-tetramethyl-4-oxopiperidine, reacting acetone with 2,2,4,4,6-pentamethyl-2,3,4,5,-tetrahydropyrimidine in the presence of a catalytically effective amount of an organic carboxylic acid halide.

17 Claims, No Drawings

PROCESS FOR PREPARING 2,2,6,6-TETRAMETHYL-4-OXOPIPERIDINE 2,2,6,6-tetramethyl-4-oxopiperidine, triacetone amine, is prepared by reacting acetone with 2,2,4,4,6-pentamethyl-2,3,4,5-tetrahydropyrimidine (acetonine). Triacetone amine has been recognized as a key intermediate in the preparation of 2,2,6,6-tetramethyl piperidyl and related light stabilizers for polymer materials.

Several procedures for reacting acetone with acetonine are described in the patents and literature.

K. Murayama U.S. Pat. No. 3,513,170, patented May 19, 1970, converts acetonine to triacetone amine by the action of a Lewis acid in the presence of water.

I. Orban U.S. Pat. No. 3,953,459, patented Apr. 27, 1976, prepares triacetone amine from acetonine by reaction with acetone or diacetone alcohol in the presence of an acidic catalyst such as boron trifluoride in a controlled amount of 0.2 to 12 mole % relative to the acetonine. The reaction can be carried out with or without water.

I. Orban U.S. Pat. No. 3,960,875, patented June 1, 1976 prepares triacetone amine by heating acetonine with acetone or diacetone alcohol in an alcohol solvent, without any catalyst.

K. Murayama U.S. Pat. No. 3,963,730, patented June 15, 1976 prepares triacetone amine from acetonine by reaction with acetone or diacetone alcohol in the presence of at least 12.5 mole % of an acid catalyst under anhydrous conditions.

In accordance with this invention, triacetone amine is prepared by a catalytic process from acetone and acetonine. Acetone and acetonine are reacted in the liquid phase in the presence of a catalytically effective amount of an organic carboxylic acid halide, and triacetone amine recovered from the reaction mixture.

Acetonine is readily prepared according to the process described by R. B. Bradbury et al, *Journal of the Chemical Society* 1947 1394. The acetonine can be in anhydrous form, or as a hydrate.

Only a small amount of the catalytically effective organic carboxylic acid halide is required. As little as 0.01% by weight of the acetonine is effective. Preferably, the amount is within the range from about 0.5% to about 10% by weight of the acetonine. Larger amounts can be used, but tend to be wasteful and uneconomic.

The organic carboxylic acid halide catalysts of this invention are mono or di carboxylic acid halides having from two to about eighteen carbon atoms, and the organic group may be substituted with halogen. They are defined by the formula:

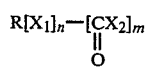

in which:

R is a hydrocarbon radical selected from the group consisting of aliphatic, cycloaliphatic and aromatic radicals having from one to about seventeen carbon atoms;

$X_1$ and $X_2$ are halogen, i.e., fluorine, chlorine, bromine, or iodine, and can be the same or different;

n is a number from 0 to 6; and m is 1 or 2.

Exemplary R aliphatic hydrocarbon include methyl, ethyl, propyl, isopropyl, butyl, isobutyl, sec-butyl, tert-butyl, amyl, isoamyl, hexyl, isohexyl, tert-hexyl, heptyl, octyl, isooctyl, tert-octyl, 2-ethylhexyl, nonyl, isononyl, decyl, isodecyl, undecyl, dodecyl, tridecyl, tetradecyl, heptadecyl, propenyl, butenyl, hexenyl, octenyl, nonenyl, heptadecenyl.

Exemplary R cycloaliphatic hydrocarbon include cyclopropyl, cyclobutyl, cyclopentyl, cyclohexyl, methyl cyclohexyl, cycloheptyl, cyclooctyl, cyclododecyl.

Exemplary R aromatic hydrocarbon include phenyl, naphthyl, phenanthryl and anthracenyl.

Exemplary organic acid halide catalysts are acetyl chloride, propionyl chloride, butyroyl chloride, octanoyl chloride, decanoyl chloride, lauroyl chloride, stearoyl chloride, diethylacetyl chloride, acetyl bromide, acryloyl chloride, methacryloyl chloride, oxaloyl dichloride, adipoyl dichloride, sebacoyl dichloride, fumaroyl dichloride, chloroacetyl chloride, dichloroacetyl chloride, trichloroacetyl chloride, bromoacetyl bromide, 3-chloropropionyl chloride, 2-bromopropionyl bromide, 2-bromopropionyl chloride, 2-bromoisobutyroyl bromide, 2-bromoisobutyroyl chloride, 2-bromo-2,2-diethylacetyl chloride, 2-bromo-2,2-diethylacetyl bromide, trifluoroacetyl chloride, 3,4-dichloroperfluoro butyroyl chloride, 3,5,6-trichloroperfluorohexanoyl chloride, 2-bromocaproyl chloride, 2-bromocaproyl chloride, 2-bromocapryloyl chloride, 2-bromononanoyl chloride, 2-bromolauroyl chloride, 2-bromopalmitoyl chloride, benzoyl chloride, benzoyl bromide, toluoyl chloride, 4-t-butylbenzoyl chloride, phthaloyl dichloride, isophthaloyl dichloride, terephthaloyl dichloride, mono and dichlorobenzoyl chloride, 2-chlorocinnamoyl chloride, cyclohexanoyl chloride.

The organic acid bromide catalysts and halogen substituted carboxylic acid halide catalysts are preferred.

A number of materials function as co-catalysts when combined with the catalyst of this invention, interacting beneficially to give synergistic results, better than with either alone.

Co-catalysts that can be used with the catalyst of this invention include elemental bromine and elemental iodine; lithium, sodium and potassium bromide and iodide; ammonium chloride, bromide and iodide; hydrazine chloride; lithium and ammonium thiocyanate; maleic hydrazide; barium hydroxide; synthetic absorbents such as magnesium silicate hydrate and aluminum silicate hydrate; boron trifluoride, zinc chloride and calcium chloride.

When a co-catalyst is used together with the catalyst of this invention, the amount of co-catalyst is usually within the range from about 0.01 to about 10% by weight of the acetone, preferably from about 0.1 to about 5%.

The relative proportions of acetonine and acetone can be varied over a wide range, from stoichiometric to a large excess of either. The molar ratio of acetonine to acetone can be within the range from about 10:1 to about 1:20, preferably from 1:3 to 1:15.

The reactants, catalyst, co-catalyst when used, solvent and other ingredients can be charged all at once, or in several increments as the reaction proceeds.

Neither reaction temperature nor reaction pressure is critical. The process of the invention will proceed at room temperature or below, as well as at elevated temperatures. Preferably, the reaction temperature is within the range from about 0° C. and the boiling point of the reaction mixture at atmospheric pressure, with a range of from about 30° to about 60° C. particularly preferred. If the reaction mixture boils at 60° C. or below, the reaction temperature can be increased to from 60° C. to 110° C. by applying superatmospheric pressure, up to about 30 atmospheres, preferably up to about 5 atmospheres.

A solvent or diluent is not necessary in the process of this invention, but can be used, if desired. The solvent should be inert, and have a boiling temperature at or above the selected reaction temperature. Solvents that can be used, for example, are aliphatic hydrocarbons, such as pentane, hexane, heptane; aromatic hydrocarbons such as benzene, toluene, xylene; chlorinated aliphatic and aromatic hydrocarbons, such as methylene chloride, trichloroethane, chloroform, carbon tetrachloride, chlorobenzene, the dichlorobenzenes and trichlorobenzenes; cycloaliphatic hydrocarbons, such as cyclohexane; aliphatic and cycloaliphatic alcohols, such as methanol, ethanol, isopropanol, butanol, t-butanol, 2-ethylhexanol, cyclohexanol; aliphatic and heterocyclic ethers, such as diethyl ether, tetrahydrofurane and dioxane.

In the preparation of triacetone amine according to the process of this invention, water does not interfere. It is neither necessary to add water, nor to exclude it.

At the end of the reaction, the lowest boiling components of the mixture are unreacted acetone and solvent, if used; these can be stripped off and used as the solvent or diluent in subsequent preparations, without separation from one another.

Triacetone amine can be recovered from the reaction mixture by precipitation as the hydrate by adding water; or by precipitation as the hydrohalide, sulfate or oxalate salt by adding the appropriate acid; or by distillation, suitably after adding an excess of strong alkali, such as concentrated aqueous potassium or sodium hydroxide solution.

The following Examples represent preferred embodiments of the invention.

EXAMPLES 1 TO 6

A flask equipped with a Dimroth condenser was charged with acetonine 77 g, acetone 174 g and 3 g of the catalyst shown in Table I. For comparison, three prior art catalysts were also used, and are reported as Controls. Then, the mixture was heated and stirred at 60° C. for five hours.

At the end of this time, the reaction mixture was stripped in vacuo, and the triacetone amine recovered by vacuum distillation. The results are shown in Table I.

TABLE I

| Example No. | Catalyst | Yield of Triacetone amine g | % |
|---|---|---|---|
| Control 1 | Ammonium chloride | 56.8 | 73.3 |
| Control 2 | Acetic acid | 42.7 | 55.1 |
| Control 3 | Monochloroacetic acid | 44.5 | 57.4 |
| Example 1 | Acetyl chloride | 74.2 | 95.7 |
| Example 2 | Acetyl bromide | 85.5 | 110.3 |
| Example 3 | Monochloroacetyl chloride | 80.0 | 103.2 |
| Example 4 | Monobromoacetyl bromide | 93.6 | 120.8 |
| Example 5 | α-Bromopropionyl bromide | 91.8 | 118.5 |
| Example 6 | Benzoyl bromide | 83.4 | 107.6 |

It is apparent that the catalysts of the invention gave much higher yields of triacetone amine than the prior art catalysts.

EXAMPLES 7 TO 11

A flask equipped with a Dimroth condenser was charged with acetonine 77 g, acetone 232 g, water 6 g and the catalyst shown in Table II, 3 g. Then, the mixture was heated and stirred at 60° C. for five hours. The reaction mixture was worked up by distillation using the same procedure as in Examples 1 to 6. The results are shown in Table II.

TABLE II

| Example No. | Catalyst | Yield of Triacetone amine g | % |
|---|---|---|---|
| Control 1 | Monochloroacetic acid | 47.8 | 61.7 |
| Example 7 | Acetyl bromide | 88.2 | 113.8 |
| Example 8 | Monochloroacetyl chloride | 84.1 | 108.5 |
| Example 9 | Monobromoacetyl bromide | 101.6 | 131.1 |
| Example 10 | Adipoyl dichloride | 80.5 | 103.9 |
| Example 11 | Benzoyl bromide | 87.0 | 112.3 |

It is apparent that the catalysts of the invention gave much higher yields of triacetone amine than the prior art catalysts.

EXAMPLES 12 TO 16

A flask equipped with a Dimroth condenser was charged with acetonine 77 g, acetone 174 g and the amount of monobromoacetyl bromide shown in Table III. The mixture was heated and stirred at 60° C. for three hours. The reaction mixture was worked up by distillation, using the same procedure as in Examples 1 to 6. The results are shown in Table III.

TABLE III

| Example No. | Amount of monobromoacetyl bromide | Yield of Triacetone amine g | % |
|---|---|---|---|
| Example 12 | 0.4 g (0.5 weight %) | 82.0 | 105.8 |
| Example 13 | 1.5 g (2 weight %) | 88.6 | 114.3 |
| Example 14 | 0.4 g (5 weight %) | 95.5 | 123.2 |
| Example 15 | 0.4 g (7.5 weight %) | 97.8 | 126.2 |
| Example 16 | 0.4 g (10 weight %) | 98.2 | 126.7 |

It is apparent that from 5 to 10 weight percent give optimum results, but that as little as 0.5 weight percent than any of the prior art catalysts tested and shown as Controls in the previous Examples.

EXAMPLES 17 TO 21

An autoclave was charged with 46.2 g of acetonine, 156.6 g of acetone and 1.5 g of the catalyst shown in Table IV. Then, the mixture was allowed to react for five hours at 60° C. while stirring. The reaction mixture was worked up as in Examples 1 to 6. The results are shown in Table IV.

TABLE IV

| Example No. | Catalyst | Yield of Triacetone amine g | % |
|---|---|---|---|
| Control 1 | Ammonium nitrate | 42.8 | 92.0 |
| Control 2 | Monochloroacetic acid | 37.4 | 80.4 |
| Example 17 | Acetyl bromide | 58.0 | 124.7 |

TABLE IV-continued

| Example No. | Catalyst | Yield of Triacetone amine | |
|---|---|---|---|
| | | g | % |
| Example 18 | Monochloroacetyl chloride | 53.2 | 114.4 |
| Example 19 | Monobromoacetyl bromide | 64.6 | 138.9 |
| Example 20 | α-Bromopropionyl bromide | 62.3 | 134.0 |
| Example 21 | Benzoyl bromide | 56.7 | 121.9 |

It is apparent that the catalysts of the invention gave much higher yields of triacetone amine than the prior art catalysts.

Having regard to the foregoing disclosure the following is claimed as the inventive and patentable embodiments thereof:

1. A process for preparing triacetone amine which comprises reacting acetone and acetonine in the liquid phase in the presence of a catalytically effective amount of an organic hydrocarbon carboxylic acid halide or organic halo-substituted hydrocarbon carboxylic acid halide selected from the group consisting of hydrocarbon mono and di carboxylic acid halides and halo-substituted hydrocarbon mono and di carboxylic acid halides having from two to about eighteen carbon atoms, and recovering triacetone amine from the reaction mixture.

2. A process according to claim 1 in which the organic group of the organic carboxylic acid halide is halo-substituted.

3. A process according to claim 1 in which the organic hydrocarbon carboxylic acid halide has the formula:

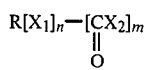

in which:
R is a hydrocarbon radical selected from the group consisting of aliphatic, cycloaliphatic and carboxylic aromatic radicals having from one to about seventeen carbon atoms;
$X_1$ and $X_2$ are selected from fluorine, chlorine, bromine, and iodine, and can be the same or different;
n is a number from 0 to 6; and
m is 1 or 2.

4. A process according to claim 1 in which the amount of organic carboxylic acid halide is at least 0.01% by weight of the acetonine.

5. A process according to claim 4 in which the amount is within the range from about 0.5% to about 10% by weight of acetonine.

6. A process according to claim 1 in which the organic carboxylic acid halide is acetyl chloride.

7. A process according to claim 1 in which the organic carboxylic acid halide is acetyl bromide.

8. A process according to claim 1 in which the organic carboxylic acid halide is chloroacetyl chloride.

9. A process according to claim 1 in which the organic carboxylic acid halide is bromoacetyl bromide.

10. A process according to claim 1 in which the organic carboxylic acid halide is bromopropionyl bromide.

11. A process according to claim 1 in which the organic carboxylic acid halide is benzoyl bromide.

12. A process according to claim 1 in which a co-catalyst reacting synergistically with the organic carboxylic acid halide is included in the reaction mixture.

13. A process according to claim 12 in which the co-catalyst is selected from the group consisting of elemental bromine and elemental iodine; lithium, sodium and potassium bromide and iodide; ammonium chloride, bromide and iodide; hydrazine chloride; lithium and ammonium thiocyanate; maleic hydrazide; barium hydroxide; magnesium silicate hydrate aluminum silicate hydrate; boron trifluoride, zinc chloride and calcium chloride.

14. A process according to claim 12 in which the amount of co-catalyst is within the range from about 0.01% to about 10% by weight of the acetone.

15. A process according to claim 1 in which the reaction temperature is within the range from about 0° C. and the boiling point of the reaction mixture at atmospheric pressure.

16. A process according to claim 15 in which the reaction temperature is within the range from about 30° to about 60° C.

17. A process according to claim 1 in which an inert solvent having a boiling temperature above the selected reaction temperature is included in the reaction mixture.

* * * * *